US00PP23568P3

(12) United States Plant Patent
Egger

(10) Patent No.: US PP23,568 P3
(45) Date of Patent: Apr. 23, 2013

(54) ***HEUCHERA* PLANT NAMED 'PEAR CRISP'**

(50) Latin Name: ***Heuchera* hybrid**
Varietal Denomination: Pear Crisp

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 83 days.

(21) Appl. No.: 13/200,483

(22) Filed: Sep. 22, 2011

(65) Prior Publication Data

US 2013/0081182 P1 Mar. 28, 2013

(51) Int. Cl.
*A01H 5/00* (2006.01)

(52) U.S. Cl.
USPC ..... Plt./440

(58) Field of Classification Search ..... Plt./440
See application file for complete search history.

*Primary Examiner* — June Hwu

(74) *Attorney, Agent, or Firm* — Klarquist Sparkman, LLP

(57) ABSTRACT

A new and distinct *Heuchera* plant substantially as shown and described, characterized by very ruffled leaves, yellow spring leaf color, lime green summer leaves, compact plant size, and short flowering stalks with small white flowers.

1 Drawing Sheet

Botanical denomination: *Heuchera* hybrid.

Variety designation: 'Pear Crisp'.

Cross reference to *Heuchera* 'Apple Crisp', applied for concurrently U.S. Plant patent application Ser. No. 13/200,484.

BACKGROUND OF THE INVENTION

The present invention relates to a new and distinct cultivar of *Heuchera* and given the cultivar name of 'Pear Crisp'. *Heuchera* is in the family Saxifragaceae. *Heuchera* 'Pear Crisp' originated from a planned cross between *Heuchera* 478-8, a proprietary unreleased plant, as the seed parent, and *Heuchera* 'Amber Waves', (U.S. Plant Pat. No. 13,348) as the pollen parent. Compared to the seed parent, *Heuchera* 478-8, the new cultivar has yellow to lime foliage rather than brown. Compared to the pollen parent, *Heuchera* 'Amber Waves', the new cultivar has leaves that are smaller more sharply ruffled and are colored yellow to lime rather than amber to tan, and flowers that are on shorter peduncles and are white rather than cream.

Compared to *Heuchera* 'Apple Crisp' (U.S. Plant patent Ser. No. 13/200,484 applied for concurrently), the new cultivar has yellow to lime foliage rather than green.

Compared to *Heuchera* 'Lime Rickey' (U.S. Plant Pat. No. 16,210), the new cultivar has a smaller habit and leaves that are smaller and more sharply ruffled.

Compared to *Heuchera* 'Lime Marmalade' (U.S. Plant Pat. No. 21,861), cultivar has a smaller habit, leaves that are smaller and more sharply ruffled, and shorter flower stalks.

This new *Heuchera* is distinguished by:

1. very ruffled leaves,
2. yellow spring leaf color,
3 lime green summer leaves,
4. compact plant size,
5. short flowering stalks with small white flowers This new cultivar has been reproduced only by asexual propagation (cuttings and tissue culture). Each of the progeny exhibits identical characteristics to the original plant. Asexual propagation by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a 6 month-old *Heuchera* 'Pear Crisp' in bloom, growing in a 4" pot in the shade house in early May in Canby, Oreg.

DETAILED PLANT DESCRIPTION

The following is a detailed description of the new *Heuchera* cultivar based on observations of six-month-old specimens grown in 4" pots in a cool greenhouse in May in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form.*—Basal rosette, herbaceous perennial.

*Hardiness.*—USDA Zone 4 to 9.

*Size.*—9 cm tall from top of the foliage to the ground and 21 cm wide.

*Habit.*—Mounding.

*Vigor.*—Good.

*Roots.*—Fibrous, freely branching, fine, and white in color; roots develop easily from cuttings.

Leaf:

*Type.*—Simple.

*Arrangement.*—Basal.

*Shape.*—Ovate.

*Lobing/division.*—5 main lobes, with 2 to 3 shallow secondary lobes.
*Venation.*—Palmate.
*Margins.*—Crenate and undulate.
*Apex.*—Mucronulate.
*Base.*—Cordate, lobes usually overlapping at the base.
*Blade size.*—Grows to 7 cm long and 6.5 cm wide.
*Surface texture.*—Top side glabrous, bottom side glandular.
*Petiole description.*—Grows to 7.5 cm long and 1.5 mm wide, glabrous, Yellow Green 145D below the leaf blade darkening to Greyed Brown 199A at the base.
*Leaf color.*—Topside Yellow Green 151C with a lighter veil of Yellow Green 154D, bottom side Yellow Green 145C; darkening to Yellow Green 145A with a lighter veil of Yellow Green 145C, bottom sided Yellow Green 145B; venation Yellow Green 145A.

Inflorescence:
*Size.*—Grows to 5 cm wide and 7 cm long.
*Type.*—Thyrse.
*Number of flowers per thyrse.*—80 to 100 per thyrse.
*Number of thyrse.*—1 in first spring bloom.
*Peduncle.*—Grows to 14 cm tall, 2 mm wide at base, Yellow Green 145A, glandular hairs, with 2 to 7 petiolate leaves (ovate, blades grow to 3 cm long and 2.4 cm wide, 3 lobed, margin biserrate, color the same as the leaves).
*Pedicel.*—Variable in size, with glandular hairs, Yellow Green 154D.
*Bloom period.*—Late April to June in Canby, Oreg.

Flower bud:
*Size.*—1.8 mm wide and 3 mm long.
*Description.*—Glandular puberulent, ovoid.
*Color.*—White 155A.

Flower:
*Type.*—Perfect.
*Shape.*—Campanulate.
*Size.*—3 mm long and 2 mm wide.
*Petal description.*—5 in number, 2 mm long and less than 1 mm wide, spatulate with a clawed base, reflexed, tip acute, margin entire, glabrous on top and bottom side, White NN155C on both sides.
*Calyx description.*—3 mm long and 2 mm wide, with 5 lobes, divided ½ way to the base, glandular hairs on outside, glabrous inside, tip obtuse, margin entire, both sides White NN155C.
*Stamen description.*—5 in number, each 2 mm long, White NN155C, anthers Yellow White 158A, no pollen, male sterile.
*Pistil description.*—One central two beaked pistil, 3 mm long, ovary 1 mm long and Yellow White 158C, style 2 mm long, White NN155C.
*Fragrance.*—None.
*Lastingness.*—Each thyrse blooms for about 2 weeks on the plant.

Fruit: None.
Seed: None.
Disease and pest tolerance: No known resistance to rust, a common problem with light leaf type *Heuchera*. Excellent disease tolerance to powdery mildew. All *Heuchera* are susceptible to root weevils.

I claim:
1. A new and distinct *Heuchera* plant as herein illustrated and described.

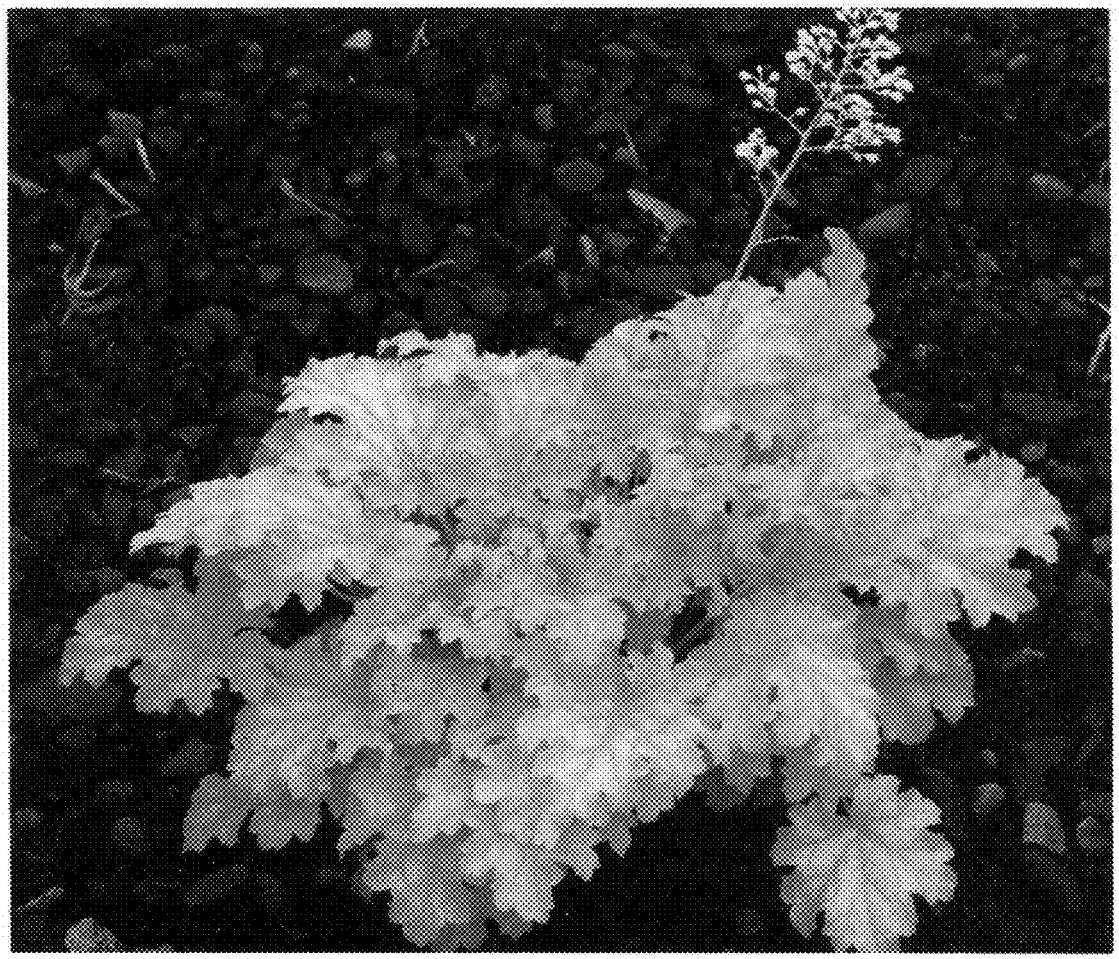

* * * * *